(12) United States Patent
Cohen et al.

(10) Patent No.: US 6,692,774 B2
(45) Date of Patent: Feb. 17, 2004

(54) SYNERGISTIC MIXTURES OF SELECTED AMINO ACIDS

(75) Inventors: Yigal Cohen, Kiryat Ono (IL); Moshe Korat, Meitar (IL); Dan Zvi-Tov, Omer (IL)

(73) Assignee: Agrogene Ltd., Kiryat Ono (IL)

( * ) Notice: Subject to any disclaimer, the term of this patent is extended or adjusted under 35 U.S.C. 154(b) by 0 days.

(21) Appl. No.: 10/146,039

(22) Filed: May 16, 2002

(65) Prior Publication Data

US 2003/0078301 A1 Apr. 24, 2003

Related U.S. Application Data

(62) Division of application No. 09/402,825, filed as application No. PCT/IL98/00167 on Apr. 8, 1998, now Pat. No. 6,414,019.

(30) Foreign Application Priority Data

Apr. 16, 1997 (IL) ................................................ 120677
Feb. 17, 1998 (IL) ................................................ 123346

(51) Int. Cl.[7] ........................ A01N 37/44; A01N 55/02; A01N 59/20
(52) U.S. Cl. ........................ 424/638; 424/630; 424/631; 424/632; 424/633; 424/634; 424/635; 424/637; 514/532; 514/534; 514/538; 514/551; 514/561; 514/563; 514/567; 514/499; 514/500
(58) Field of Search ................................. 514/563, 567, 514/561, 532, 534, 538, 551, 499, 500; 424/630–635, 637–638

(56) References Cited

FOREIGN PATENT DOCUMENTS

| WO | WO 95/15684 | 6/1995 |
|----|-------------|--------|
| WO | WO 96/22690 | 8/1996 |

OTHER PUBLICATIONS

Cohen, Yigal, "Local and systemic control of Phytophthora infestans in tomato plants by DL–3–amino–n–butanoic acids," Phytopathology, vol. 84, No. 1, 1993, pp. 5–59.*
The Agrochemicals Handbook, The Royal Society of Chemistry, Unwin Brothers Ltd., Old Working, Surrey, United Kingdom, 1983, p. A245/Oct. 83.*
Ryals et al., "Systemic Acquired Resistance", The Plant Cell, vol. 8, pp. 1809–1819, 1996.
Gisi et al., "Synergistic Interaction of Fungicides in Mixtures", Pyhtopathology, vol 86, No. 11, pp. 1273–1279, 1996.
Cohen et al., "β–Aminobutyric Acid Induces the Accumulation of Pathogenesis–Related Proteins in Tomato (*Lycopersicon esculenttum* L.) Plant and Resistance to Late Blight Infection Caused by *Pytophthora infestans*", Plant Physoil., vol. 104, pp. 59–66, 1994.
Tomlin, "The Pesticide Manual Incorporating the Agricultural Handbook", 10th Ed. pp. 635–636, 1995.

* cited by examiner

Primary Examiner—John Pak
(74) Attorney, Agent, or Firm—Browdy and Neimark, P.L.L.C.

(57) ABSTRACT

Novel synergistic fungicidal compositions used for protecting seeds, plants and other vegetative material against fungi contain a mixture of one or more compounds selected from group A and one or more compounds selected from group B. Compounds from group A are selected from β-Amino butyric acid and its N-benzoyl-octyl ester derivatives. Compounds from group B are selected from the group of fosetyl aluminum, dimethomorph, a mixture of folpet and ofurace (45:5), folpet, fencaramid (Bayer SZX), mancozeb, cymoxanil, methalaxyl, the single optical isomer of metalaxyl, a mixture of cymoxanil and mancozeb (4:1), copper sulfate, copper hydroxide, copper sulfate hydrate, azoxystrobin, and acibenzolar-s-methyl.

10 Claims, No Drawings

SYNERGISTIC MIXTURES OF SELECTED AMINO ACIDS

This is a division of copending parent application Ser. No. 09/402,825 now U.S. Pat. No. 6,414,019, the U.S. National Stage (371) of PCT/IL98/00167, filed Apr. 8, 1998.

INTRODUCTION

The present invention concerns synergistic fungicidal mixtures. The present invention more particularly concerns synergistic mixture of β-aminobutyric acid (hereinafter referred to as BABA) and its N-benzoyl-octyl ester derivatives for the control of plant diseases.

BACKGROUND OF THE INVENTION

Fungicides are often combined in mixtures for 3 main reasons: 1. to widen the spectrum of antifungal activity to control several diseases occurring simultaneously in a crop 2. to exploit synergistic interaction between fungicides, by which the overall activity is increased and the concentration of the compounds reduced, and 3. to delay the selection process of resistant fungal individuals to one component of the mixture (Gisi, Phytopathology 86 1273–1279, 1996).

Avoidence of plant disease in agricultural production may be accomplished not only by using fungicides or fungicidal mixtures but also by using "plant activators", molecules which enhance the natural resistance (defense) of the plant. Such activators which have no direct fungicidal effect on the pathogen (Ryals et al The Plant Cell 8: 1809–1819, 1996), induce systemic acquired resistance (SAR) in the plant several days after application (Ibid).

To date only few molecules were reported to induce SAR in crop plants viz. salicylic acid (SA), 2,6-dichloroisonicotinic acid (INA) benzol (1,2,3) thiadiazole-7-carbothiouic acid S-methyl ester (BTH) (Ibid), and DL-3-amino butyric acid (BABA, Cohen et al Plant Physiology 104: 56–59, 1994).

However whereas SA, INA or BTH have to be applied to the crop ahead of infestation (Ryals, et al Ibid) BABA can be applied post—infectionaly (Cohen et al Ibid).

The idea behind the present invention is to combine two methods of disease control—the direct—kill method operating on the target pathogen and the indirect method of activating the natural defense approach of the crop plant. Such two methods are combined by using mixtures of a fungicide or fungicides (direct—kill) with BABA or its N-benzoyl-octyl ester derivative(SAR).

We show here that such mixtures are synergistic in controlling plant diseases.

OBJECTIVES OF THE INVENTION

It is the objective of the present invention to provide novel mixtures of fungicides of β-aminobutyric acids. It is an objective of the present invention to provide a synergistic mixture of BABA and/or its N-benzoyl-octyl ester derivative with various other fungicides.

SUMMARY OF THE INVENTION

In accordance with the present invention there is provided synergistic fungicidal compositions comprising one or more compounds selected from Group A and one or more compounds selected from Group B, wherein the compounds of Group A are selected from the group consisting of DL-3 aminobutyric-acid and its N-Benzoyl octyl ester, and the compounds of Group B are selected from the group consisting of fosetyl aluminum, dimethomorph, a mixture of folpet and ofturace (45:5), folpet, fencaramid (Bayer SZX), mancozeb, cymoxanil, methalaxyl, the single optical isomer of metalaxyl, a mixture of cymoxamil and mancozeb (4:1), copper sulfate, copper hydroxide, copper sulfate hydrate, azoxystrobin, and acibenzolar-s-methyl.

The present invention also provides an improved method of controlling fungi, especially late blight and downy mildews, applying to the plant a composition containing an effective amount of one of these mixtures. The present invention further provides an improved method of controlling *phytophthora infertan* in potato or tomatoe, *Pseudoperonospora cubensis* in cucumber or melon, *Plasmopera viticola* in grapes, and *Peronospora tabacina* in tabacco.

DETAILED DESCRIPTION OF THE INVENTION

Methodology

Plants 1. Potato (cultivar Alpha) were grown from tubers in 1 liter pots in sandy soil in the greenhouse. At 5 weeks after planting when they had several shoots in a pot, with 10–12 leaves per shoot, plants were taken for assays.

2. Cucumber (cultivate Dlila) plants were grown from seed in 0.251 liter pots containing sandy soil in the greenhouse. At 3 weeks after sowing, when they developed 2 leaves they were used.

3. Grapes (cultivate Superior) plants were grown from cuttings (first in perlite and then in sandy soil) in pots in the greenhouse. At 8 weeks after planting leaves were detached for experiments.

Fungal Pathogens. Potatoes were inoculated with sporangic of *Phytophthora infestans* (resistant to metalaxyl). Cucumbers were inoculated with sporangia of *Pseudoperonospora cubensis* (resistance to metalaxyl). Grapes were inoculated with *Plasmopara viticola* Chemicals.

1. DLβ-amino-butanoic acid (BABA)
2. DL-4-benzoyl-3-amino butanoic acid octylester (039-81)
3. Cymoxanil (Curzate)
4. phosetyl-aluminium (Alliette)
5. Mancozeb
6. Folpet
7. Metalaxyl, metalaxyl-Gold
8. Copper sulphate, copper hydroxide
9. (Mancozeb+dimethomorph, prepacked 600 g+90 g a.i. per 1 kg)
10. (Mancozeb+metalaxyl, prepacked 560 g+75 g a.i. per 1 kg)
11. Folpet+ofurace, 450 g+60 g a.i. per 1 kg)
12. Bayer-SZX (Fencaramid)
13. Mancozeb+Cymoxanil (4:1)
14. Azoxystrobin
15. Acibenzolar-s-methyl
16. Dimethomorph Except BABA which was dissolved in water, all other chemicals or prepacked mixtures produced a suspension or emulsion in water.

Spraying The chemicals were sprayed onto the upper leaf surfaces of either potatoes or cucumbers with the aid of a fine glass atomizer. Control plants were sprayed with water. Experiments with grapes were carried out using 12 mm leaf discs floating on 1 ml of the test compound(s) in 24-well titer plates, upperside down.

Inoculation

Potatoes and cucumbers were inoculated one day after spraying. Grape leaf discs were inoculated soon after floating. Inoculation of potato was done by spraying the upper leaf surfaces of the plants with a sporangial suspension containing 2000 sporangia/ml. Sporangia were harvested 0.5 h before inoculation from infected potato tuber slices. Cucumbers were sprayed with a sporangial suspension containing 1500 sporangia/ml. Sporangia were harvested from infected cucumber plants kept in humid growth chambers (at 15° C.). Leaf discs of grapes were inoculated with 2 sporangial droplets containing each 300 sporangia. Sporangia were harvested from infected leaves kept in petri dishes on wet filter paper at 15° C. Inoculated plants or titer plates were placed in a dew chamber at 18° C. overnight and then transferred to a growth chamber at 20° C. (12 h light/day 100 pE.m$^{-2}$.S$^{-1}$) for symptom production (late blight in potato and downy mildew in cucumber), or for sporulation of *P. viticola* in grape leaf discs.

General Procedure for Tabacco

One month old tobacco plants (cv.xanthi nc.). were sprayed onto their foliage with the test compounds. Two days later they were inoculated with 10$^4$ spores/ml of *Perouospora latacin* of either the S or the R strain. Inoculated plants were placed in 100% relative humidity over night and then incubated at 20° C. with 12 h light/day. A week after innoculation plants were again placed at 100%-RH at 18° C. in the dark to induce fungal sporulation. Sporulation was quantitated by removing 2 cm$^2$ leaf discs from each leaf and counting with the aid of a haemocytometer. The extent of sporulation inhibition was calculated relative to that in control (untreated) inoculated plants. Ed$_{go}$ was computed after linear regression and of was calculated according to Wadely.

General Procedure for Grapes

Leaf discs (2-cm$^2$) were removed from the top leaves of grape plants (cv. Superior) grown in the greenhouse. Discs were floated (lower surface uppermost on the test solutions over filter paper of 9 cm diameter). Petri dishes. Leaf discs were immediately innoculated with 2 (10 ml) droplets of sporangial suspension (10$^4$/ml) of *Plasmopara viticola* per disc. Dishes were inculcated at 20° C. with 12 h light/day for 10 days until fungal sporulation was quantified.

Disease Assessment

At the time intervals post inoculation specified in the Examples, infected leaf area in potato and cucumber was assessed visually. In control inoculated plants most or all of the foliage (80–100%) was devastated by the disease. Percentage control of the disease by a chemical treatment was calculated as % control=(1−x/y)×100 whereas x=proportion leaf area diseased in treated plants
and
y=proportion leaf area diseased in control plants.

In grapes, proportion of leaf discs showing sporulation were similarly used.

Calculation of Control Efficacy and Synergism

Each chemical and each mixture was applied to plants at various doses of the active ingredient. Dose—response curves were produced and transferred to log—dose probit response curves as described by Kosman and Cohen (Phytopathology 86: 1263–1272, 1996). ED$_{90}$ values (dose required for achieving 90% control of the disease) taken from the log-probit 7 curves were used to calculate the Cotoxicity Factor (CF) according to the Wadely procedure (Kosman and Cohen, Ibid; Gisi phytopatcology 86: 1273–1279, 1966). "CF" is defined as the ratio between the expected dose and the observed dose that provide the same level of disease control (Kosman and Cohen, Ibid). The observed dose of each component of a mixture is taken from the experiment and the expected dose of all mixture made of that components is calculated by the Wadely formula:

$$ED_{90} \text{ expected} = \frac{a+b}{\frac{a}{ED_{90} \text{ obs.}A} + \frac{b}{ED_{90} \text{ obs.}B}}$$

where a and b are the absolute amounts of the components A and B in a mixture and ED$_{90}$. obs.A and Ed$_{90}$ obs.B are the ED$_{90}$ values of A and B obtained by the experiment. CF values of>2.0 are considered to represent a strongly synergistic mixture (Gisi, Ibid).

According to a further feature of the invention, there is provided a fungicidal composition which comprises a compound of the invention together with carrier. The active compound can be employed as a wide variety of formulations, for example as an aqueous dispersion, a dispersible powder, as seed dressing, granules or dust. As a dispersion the composition comprises an active compound together with a dispersing agent dispersed in a liquid medium, preferably water. It can be in a form of a concentrated primary composition which requires dilution with a suitable quantity of water or other diluent before application. Such primary compositions are a convenient way of supplying the consumer and preferred example is a dispersible powder. A dispersible powder comprises an active compound, a dispersing agent and solid carrier. The latter can be, for example, kaolin, talc, or diatomaceous earth and in addition, the dispersible powder can contain a wetting agent.

Other formulations include seed dressing, granules or dusts, in all of which the active compound is associated with a solid carrier and which are intended for direct application. They can be made by methods well known in the art. Preferably all compositions comprising a solid carrier are made by mixing the active compound in particulate form with a particulate carrier.

The concentration of the active compound in the composition of the inventioncan vary widely. In the case of a primary composition it is preferably from 15% to 95% by weight, more especially from 50% to 80% by weight. A composition intended for direct application to a crop preferably comprises from 0.001% to 10% more, especially from 0,005% to 5% by weight of the active compound, although the aerial spraying of a crop is contemplated compositions having higher concentrations, for example up to 30% by weight may be chosen in preference.

The fungicidal composition of the present invention may be applied as a ready-mixed composition, as a tank mix, or applying the compounds of each group separately.

Following the methods outlined above numerous mixtures were prepared and their activity against a variety of diseases were studied. The results of 35 studies are listed in Tables 1–35.

While the invention will now be described in connection with certain preferred embodiments in the following examples it will be understood that it is not intended to limit the invention to these particular embodiments. On the contrary, it is intended to cover all alternatives, modifications and equivalents as be included within the scope of the invention, as defined by the appended claims. Thus, the following examples which iclude preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

TABLE 1

CONTROL OF LATE BLIGHT IN POTATO BY BABA COPPER SULFATE HYDRATE MIXTURE[a]

| Compounds | Ratio | Percent Disease Control[b] mg/L Active Ingredient | | | | | | $ED_{90}$ mg/L | CF |
|---|---|---|---|---|---|---|---|---|---|
| | | 2 | 8 | 32 | 125 | 250 | 1000 | | |
| BABA | — | — | — | 0 | 0 | 0 | 13 | 2678 | — |
| $Cu^{+2}$ | — | 0 | 0 | 63 | 83 | — | — | 143 | — |
| BABA + $Cu^{+2}$ | 80 + 20 | 0 | 0 | 13 | 88 | — | — | 126 | 4.7 |
| | 70 + 30 | 0 | 0 | 50 | 93 | — | — | 101 | 4.2 |
| | 60 + 40 | 0 | 0 | 85 | 93 | — | — | 85 | 3.9 |

[a]5 days post inoculation
[b]Control plants showed 100% leaf blight

TABLE 2

CONTROL OF LATE BLIGHT IN POTATO BY BABA CYMOXANIL MIXTURE (CURZATE[R])[a]

| Compounds | Ratio | Percent Disease Control[b] mg/L Active Ingredient | | | | | $ED_{90}$ mg/L | CF |
|---|---|---|---|---|---|---|---|---|
| | | 4 | 16 | 62 | 250 | 1000 | | |
| BABA | — | — | 3 | 24 | 18 | 64 | 1498 | — |
| Cymoxanil | — | 36 | 73 | 64 | 98 | — | 128 | — |
| BABA + | 80 + 20 | 9 | 9 | 3 | 79 | — | 294 | 1.6 |
| Cymoxanil | 50 + 50 | 73 | 76 | 82 | 98 | — | 114 | 2.1 |

[a]5 days post inoculation
[b]Control plants showed 83% leaf blight

TABLE 3

CONTROL OF LATE BLIGHT IN POTATO BY BABA FOSETYL ALUMINUM MIXTURE[a]

| Comounds | Ratio | Percent Disease Control[b] mg/L Active Ingredient | | | | $ED_{90}$ mg/L | CF |
|---|---|---|---|---|---|---|---|
| | | 16 | 62 | 250 | 1000 | | |
| Cultivar Cara[b] | | | | | | | |
| BABA | | 9 | 9 | 9 | 24 | 3233 | — |
| Fosetyl – Al | | 9 | 24 | 24 | 70 | 1390 | — |
| BABA + | 75 + 25 | 9 | 9 | 39 | 70 | 1311 | 1.9 |
| Fosetyl – Al | 25 + 75 | 9 | 9 | 39 | 79 | 1142 | 1.4 |
| Cultivar Draga[c] | | | | | | | |
| BABA | | 0 | 0 | 0 | 53 | 1533 | — |
| Fosetyl – Al | | 33 | 33 | 50 | 93 | 856 | — |
| BABA + | 75 + 25 | 67 | 67 | 93 | 93 | 639 | 1.7 |
| Fosetyl – Al | 25 + 75 | 0 | 0 | 93 | 100 | 245 | 3.9 |

[a]5 days post inoculation
[b]Contact plants showed 83% leaf blight
[c]Contact plants showed 38% leaf blight

TABLE 4

CONTROL OF LATE BLIGHT IN POTATO BY BABA MIXTURES OF MANCOZEB + DIMETHOMORPH MIXTURES[a]

| Compounds | Ratio | Percent Disease Control[b] mg/L Active Ingredient | | | | | $ED_{90}$ mg/L | CF |
|---|---|---|---|---|---|---|---|---|
| | | 4 | 16 | 62 | 250 | 1000 | | |
| BABA | — | — | 3 | 24 | 18 | 64 | 1498 | — |
| MANCOZEB + DIMETHOMORPH | — | 70 | 73 | 82 | 98 | — | 115 | — |
| BABA + (MANCOZEB[c] + DIMETHOMORPH) | 80 + 20 | 64 | 73 | 70 | 82 | — | 287 | 1.5 |
| | 50 + 50 | 85 | 70 | 70 | 91 | — | 189 | 1.1 |

[a]5 days post inoculation
[b]Control plants showed 83% leaf blight
[c]60% Mancozeb & 9% Dimethomorph

TABLE 5

CONTROL OF LATE BLIGHT IN POTATO BY BABA FOLPET/OFURACE (45 + 5) MIXTURE[a]

| Compounds | Ratio | Percent Disease Control[b] @ mg/L Active Ingredient - | | | | | $ED_{90}$ mg/L | CF |
|---|---|---|---|---|---|---|---|---|
| | | 4 | 16 | 62 | 250 | 1000 | | |
| BABA | — | — | 14 | 14 | 14 | 36 | 2617 | |
| FOLPET/ OFURACE | | 77 | 89 | 99 | 100 | — | 19 | |
| BABA + (FOLPET/ OFURCE) | 50 + 50 | 74 | 81 | 99 | 100 | — | 22 | 1.8 |

[a]7 days
[b]Control plants showed 88% leaf blight

TABLE 6

CONTROL OF LATE BLIGHT IN POTATO BY BABA FOLPET - CYMOXANIL MIXTURE[a]

| Compounds | Ratio | Percent Disease Control[b] mg/L Active Ingredient | | | | $ED_{90}$ mg/L | CF |
|---|---|---|---|---|---|---|---|
| | | 16 | 62 | 250 | 1000 | | |
| BABA | | 22 | 22 | 22 | 69 | 1481 | |
| FOLPET | | 81 | 95 | 98 | 100 | 84 | |
| CYMOXANIL | | 83 | 86 | 91 | 100 | 183 | |
| BABA + FOLPET + CYMOXANIL | 60 + 25 + 15 | 72 | 89 | 98 | 100 | 95 | 2.5 |
| | 25 + 60 + 15 | 92 | 86 | 95 | 100 | 104 | 1.3 |

[a]6 day post innoculation
[b]Control plants showed 80% leaf blight

TABLE 7

CONTROL OF LATE BLIGHT IN POTATO BY THE N-BENZOYL OCTYL ESTER OF BABA AND FENCARAMID[a]

| Compounds | Ratio | Percent Disease Control mg/L Active Ingredient[b] | | | | | | | $ED_{90}$ mg/L | CF |
|---|---|---|---|---|---|---|---|---|---|---|
| | | 2 | 8 | 32 | 125 | 250 | 1000 | 2000 | | |
| BABA Derivative | — | — | — | — | 15 | 25 | 50 | 53 | 2395 | |
| Fencaramid | | 0 | 50 | 98 | 100 | — | — | — | 19 | |
| BABA |

TABLE 7-continued

CONTROL OF LATE BLIGHT IN POTATO BY THE
N-BENZOYL OCTYL ESTER OF BABA AND FENCARAMID[a]

| Compounds | Ratio | 2 | 8 | 32 | 125 | 250 | 1000 | 2000 | ED$_{90}$ mg/L | CF |
|---|---|---|---|---|---|---|---|---|---|---|
| DERIVATIVE + FENCARAMID | 80 + 20 | 44 | 63 | 85 | 100 | — | — | — | 31 | 3.0 |
|  | 90 + 10 | 13 | 50 | 56 | 94 | — | — | — | 97 | 1.8 |

Percent Disease Control mg/L Active Ingredient[b]

[a]4 day post inoculation
[b]Control plants at 100% leaf blight

TABLE 8

CONTROL OF LATE BLIGHT IN POTATO BY N-BENZOYL
OCTYL ESTER OF BABA, Cu (OH)$_2$ (as 50% a.i), MANCOZEB[a]

| Compounds | Ratio | 4 | 16 | 62 | 250 | 1000 | ED$_{90}$ mg/L | CF |
|---|---|---|---|---|---|---|---|---|
| N-benzoyl octyl ester derivative of BABA | — | 3 | 25 | 25 | 75 | 1261 |  |
| Cu(OH)$_2$ |  | 0 | 0 | 13 | 75 | — | 298 |  |
| Cu(OH)$_2$ + Mancozeb | 70 + 30 | 0 | 3 | 44 | 50 | — | 416 |  |
| N-benzoyl octyl ester derivative of BABA + Cu(OH)$_2$ | 80 + 20 | 3 | 3 | 25 | 75 |  | 300 | 2.6 |
| N-benzoyl octyl ester derivative of BABA + Cu(OH)$_2$ + mancozeb | 80 + :14 + 6 | 3 | 3 | 75 | 83 |  | 239 | 3.8 |

Percent Disease Control[b] mg/L Active Ingredient

[a]7 days innoculation
[b]Control plants showed 100% leaf blight

TABLE 9

CONTROL OF LATE BLIGHT IN POTATO BY
N-BENZOYL OCTYL ESTER DERIVATIVE OF
FOLPET/OFURACE (45 + 5) AND THEIR MIXTURES[a]

| Compounds | Ratio | 4 | 16 | 62 | 250 | 1000 | ED$_{90}$ mg/L | CF |
|---|---|---|---|---|---|---|---|---|
| N-benzoyl octyl ester derivative of BABA | — | 0 | 0 | 0 | 25 |  | 2011 |  |
| Folpet + Ofurace (9 + 1) |  | 0 | 0 | 3 | 73 | — | 301 |  |
| N-benzoyl octyl ester derivative of BABA + (Folpet Ofurace | 67 + 33 | 0 | 13 | 75 | 100 | — | 74 | 9.5 |
|  | 50 + 50 | 8 | 8 | 69 | 100 | — | 82 | 6.4 |
|  | 33 + 67 | 3 | 19 | 75 | 98 | — | 15 | 3.6 |

Percent Disease Control @ mg/L Active Ingredient[b]

[a]7 days post inoculation
[b]Control plants showed 100% leaf blight

TABLE 10

CONTROL OF LATE BLIGHT IN POTATO BY
N-BENZOYL OCTYL ESTER DERIVATIVE OF BABA,
AND MANCOZEB + CYMOXANIL; 4:1 AND THEIR MIXTURES[a]

| Compounds | Ratio | 4 | 16 | 62 | 250 | 1000 | ED$_{90}$ mg/L | CF |
|---|---|---|---|---|---|---|---|---|
| N-benzoyl octyl ester derivative of BABA | — | 0 | 0 | 0 | 25 |  | 2011 |  |
| Mancozeb + Cymoxanil |  | 0 | 25 | 25 | 75 | — | 313 |  |
| N-benzoyl octyl ester derivative of BABA + Mancozeb + Cymoxanil | 67:33 | 25 | 68 | 70 | 95 | — | 169 | 4.3 |
|  | 50:50 | 5 | 63 | 88 | 98 | — | 95 | 5.7 |
|  | 33:67 | 25 | 69 | 90 | 100 | — | 52 | 8.3 |

Percent Disease Control[b] mg/L Active Ingredient

[a]7 days Post innoculation
[b]Control plants showed 100% leaf blight

TABLE 11

CONTROL OF LATE BLIGHT IN POTATO BY N-BENZOYL OCTYL
ESTER DERIVATIVE OF BABA, FOLPET AND THEIR MIXTURES[a]

| Compounds | Ratio | 4 | 16 | 62 | 250 | 500 | 1000 | 2000 | ED$_{90}$ mg/L | CF |
|---|---|---|---|---|---|---|---|---|---|---|
| N-benzoyl octyl ester derivative of BABA |  | — | — | — | 63 | 69 | 85 | 89 | 1514 |  |
| Folpet |  | 70 | 75 | 90 | 95 | — | — | — | 141 |  |
| N-benzoyl octyl ester derivative of BABA + Folpet | 80 + 20 | 50 | 80 | 85 | 93 | — | — | — | 167 | 3.1 |
|  | 67 + 33 | 13 | 76 | 86 | 96 | — | — | — | 130 | 2.8 |
|  | 33 + 67 | 63 | 76 | 78 | 88 | — | — | — | 224 | 0.9 |
|  | 20 + 80 | 25 | 75 | 73 | 97 | — | — | — | 140 | 1.2 |

Percent Disease Control[b] mg/L Active Ingredient

[a]4 days post inoculation
[b]Control plants showed 100% leaf blight

TABLE 12

CONTROL OF LATE BLIGHT IN POTATO BY N-BENZOYL OCTYL ESTER DERIVATIVE OF BABA, FENCARAMID (BAYER SZX) AND THEIR MIXTURES[a]

| Compounds | Ratio | 2 | 8 | 31 | 25 | 500 | 1000 | 2000 | $ED_{90}$ mg/L | CF |
|---|---|---|---|---|---|---|---|---|---|---|
| N-benzoyl octyl ester derivative of BABA | — | — | — | — | 15 | 25 | 50 | 53 | 3204 | — |
| Fencaramid | | 0 | 50 | 98 | 100 | — | — | — | 19 | — |
| N-benzoyl octyl ester derivative of BABA + Fencarmid | 90:10 | 13 | 50 | 56 | 94 | — | — | — | 83 | 2.2 |
| | 80:20 | 44 | 63 | 85 | 100 | — | — | — | 31 | 3.0 |

[a]5 days post innoculation
[b]Control plants showed 100% leaf blight

TABLE 13

CONTROL OF DOWNY MILDEW IN CUCUMBER BY BABA, COPPER SULPHATE HYDRATE (EXPRESSED AS mg/L $Cu^{++}$) AND THEIR MIXTURES[a]

| Compounds | Ratio | 16 | 62 | 250 | 1000 | $ED_{90}$ mg/L | CF |
|---|---|---|---|---|---|---|---|
| BABA | | 43 | 43 | 57 | 72 | 1468 | |
| | | 2 | 8 | 32 | 125 | | |
| $Cu^{++}$ | | 57 | 72 | 80 | 89 | 105 | |
| BABA + $Cu^{++}$ | 80 + 20 | 72 | 72 | 86 | 89 | 102 | 4.0 |
| | 70 + 30 | 57 | 72 | 72 | 89 | 111 | 2.7 |
| | 60 + 40 | 57 | 72 | 86 | 89 | 102 | 1.9 |

[a]7 days post innoculation
[b]Control plants showed 88% leaf infection

TABLE 14

CONTROL OF DOWNY MILDEW IN CUCUMBER BY BABA, (EXPRESSED AS $Cu(OH)_2$) ($Cu(OH)_2$ + MANCOZEB) AND THEIR MIXTURES

| Compounds | Ratio | 4 | 16 | 62 | 250 | 1000 | $ED_{90}$ mg/L | CF |
|---|---|---|---|---|---|---|---|---|
| BABA | | — | 33 | 33 | 50 | 67 | 1576 | |
| $Cu(OH)_2$ | | 67 | 67 | 77 | 80 | — | 304 | |
| $Cu(OH)_2$ + mancozeb | 70 + 30 | 67 | 67 | 83 | 93 | — | 174 | |
| BABA + $Cu(OH)_2$ | 80 + 20 | 67 | 70 | 77 | 90 | — | 210 | 4.1 |
| BABA + $Cu(OH)_2$ + mancozeb | 80 + 14 + 6 | | 70 | 70 | 90 | 90 | 191 | 3.2 |

[a]4 days post innoculation
[b]Control plants were 83% infected

TABLE 15

CONTROL OF DOWNY MILDEW IN CUCUMBER BY BABA (FOLPET/OFURACE 45 + 5)

| Compounds | Ratio | 4 | 16 | 62 | 250 | 1000 | $ED_{90}$ mg/L | CF |
|---|---|---|---|---|---|---|---|---|
| BABA | | — | 0 | 29 | 57 | 71 | 1273 | — |
| Vamin | | 43 | 57 | 71 | 91 | — | 206 | — |
| BABA + Vamin | 67 + 33 | 14 | 21 | 57 | 97 | — | 166 | 2.8 |
| | 50 + 50 | 14 | 43 | 71 | 89 | — | 217 | 2.1 |
| | 33 + 67 | 29 | 57 | 74 | 89 | — | 214 | 1.3 |

[a]7 days post innoculation
[b]Control plants were 88% infected

TABLE 16

CONTROL OF DOWNY MILDEW CUCUMBER BY BABA AND (MANCOZEB + CYMOXANIL; 4:1)

| Compounds | Ratio | 4 | 16 | 62 | 250 | 1000 | $ED_{90}$ mg/L | CF |
|---|---|---|---|---|---|---|---|---|
| BABA | — | | 0 | 29 | 57 | 71 | 1273 | — |
| (Mancozeb + Cymoxanil) | | | 14 | 80 | 97 | 100 | 33 | — |
| BABA + (Mancozeb + Cymoxanil) | 67 + 33 | 21 | 57 | 77 | 97 | — | 135 | 0.7 |
| | 50 +:50 | 57 | 74 | 100 | 100 | — | 20 | 3.2 |
| | 33 +:67 | 29 | 94 | 100 | 100 | — | 14 | 3.5 |

[a]7 days post innoculation
[b]Control plants were 88% infected

TABLE 17

CONTROL OF DOWNY MILDEW IN CUCUMBER BY BABA + (MANCOZEB + METALAXYL)

| Compounds | Ratio | 4 | 16 | 62 | 250 | 1000 | $ED_{90}$ mg/L | CF |
|---|---|---|---|---|---|---|---|---|
| BABA | | — | 0 | 15 | 3 | 59 | 1443 | — |
| Mancozeb + Metalaxyl | | 34 | 53 | 71 | 82 | — | 268 | — |
| BABA + Mancozeb + Metalaxyl | 88 + 12 | 0 | 0 | 9 | 96 | — | 221 | 4.3 |
| | 75 + 25 | 18 | 44 | 53 | 81 | — | 281 | 2.4 |
| | 50 + 50 | 38 | 76 | 76 | 96 | — | 150 | 3.0 |

[a]6 days post innoculation
[b]Control plants were 88% infected

TABLE 18

CONTROL OF DOWNY MILDEW IN CUCUMBER BY BABA, FOLPET & METALAXYL[a] 87:13)

| Compounds | Ratio | 4 | 16 | 62 | 250 | 1000 | mg/LF | CF |
|---|---|---|---|---|---|---|---|---|
| BABA | | — | 0 | 15 | 3 | 59 | 1443 | — |
| Folpet & Metalaxy (87 + 13) | | 0 | 0 | 56 | 76 | — | 280 | — |
| BABA + [Folpet + metalaxyl] | 88 + 12 | 12 | 0 | 59 | 81 | — | 260 | 3.7 |
| | 75 + 25 | 68 | 53 | 56 | 71 | — | 393 | 1.8 |
| | 50 + 50 | 0 | 38 | 62 | 68 | — | 339 | 1.4 |

[a]6 days post innoculation
[b]Control plants were 88% infected

TABLE 19

CONTROL OF DOWNY MILDEW IN CUCUMBER BY BABA; FOLPET & METALAXYL[a], (7 + 1) (MANCOZEB + METALAXYL), (FOLPET + OFURACE) AND THEIR MIXTURES

| Compounds | Ratio | Percent Disease Control[b] mg/L Active Ingredient | | | | | $ED_{90}$ mg/L | CF |
|---|---|---|---|---|---|---|---|---|
| | | 4 | 16 | 62 | 250 | 1000 | | |
| BABA | — | | 12 | 19 | 25 | 31 | 3218 | |
| Folpet + metalaxyl | | 62 | 82 | 90 | 97 | — | 112 | |
| BABA + [Folpet + metalaxyl] | 80:20 | 62 | 70 | 80 | 85 | — | 247 | 2.0 |
| | 50:50 | 75 | 77 | 80 | 97 | — | 133 | 1.6 |
| (Mancozeb + metalaxyl) | | 77 | 85 | 95 | 97 | — | 100 | — |
| BABA (Mancozeb + metalaxyl) | 80 + 20 | 82 | 87 | 92 | 97 | — | 105 | 4.2 |
| | 50 + 50 | 82 | 92 | 97 | 97 | — | 92 | 2.1 |
| (Folpet + Ofurace) | | 37 | 50 | 62 | 82 | — | 279 | — |
| BABA + (Folpet + Ofurace) | 80:20 | 50 | 62 | 80 | 92 | — | 187 | 5.5 |
| | 50:50 | 77 | 97 | 92 | 100 | — | 33 | 15.6 |

[a] 7 days post innoculation
[b] Control plants were 100% infected

TABLE 20

CONTROL OF DOWNY MILDEW IN CUCUMBER BY BABA, METALAXYL SINGLE ISOMER MANCOZEB AND THEIR MIXTURES[a]

| Compounds | Ratio | Percent Disease Control[b] mg/L Active Ingredient | | | | | $ED_{90}$ mg/L | CF |
|---|---|---|---|---|---|---|---|---|
| | | 4 | 16 | 62 | 250 | 1000 | | |
| BABA | — | | 8 | 8 | 8 | 38 | 2155 | |
| mancozeb | | 0 | 8 | 23 | 72 | — | 315 | |
| Metalaxyl Single Isomer | | 0 | 0 | 0 | 8 | — | 844 | |
| BABA + mancozeb + Metalaxyl Single Isomer | 55 + 40 + 5 | 23 | 23 | 54 | 75 | — | 313 | 2.0 |
| | 50 + 40 + 10 | 38 | 25 | 31 | 80 | — | 314 | 2.0 |
| | 40 + 40 + 20 | 8 | 15 | 8 | 31 | — | 689 | 0.9 |
| | 45 + 50 + 5 | 8 | 8 | 54 | 72 | — | 309 | 1.7 |
| | 40 + 50 + 10 | 8 | 31 | 54 | 89 | — | 228 | 2.3 |
| | 30 + 50 + 10 | 8 | 15 | 31 | 83 | — | 273 | 1.9 |
| | 35 + 60 + 5 | 54 | 54 | 78 | 86 | — | 239 | 2.0 |
| | 30 + 60 + 10 | 46 | 38 | 54 | 85 | — | 268 | 1.7 |
| | 20 + 60 + 20 | 61 | 69 | 69 | 83 | — | 281 | 1.6 |
| | 25 + 70 + 5 | 38 | 46 | 78 | 97 | — | 139 | 3.0 |
| | 20 + 70 + 10 | 38 | 23 | 63 | 94 | — | 194 | 2.1 |
| | 10 + 70 + 20 | 38 | 69 | 23 | 78 | — | 362 | 1.1 |

[a] 6 days post innoculation
[b] Control plants were 81% infected

TABLE 21

CONTROL OF DOWNY MILDEW IN CUCUMBER BY BABA, ALIETTE, CYMOXANIL AND THEIR MIXTURES

| Compounds | Ratio | Percent Disease Control[a] mg/L Active Ingredient | | | | $ED_{90}$ mg/L | CF |
|---|---|---|---|---|---|---|---|
| | | 16 | 62 | 250 | 1000 | | |
| BABA | | 37 | 67 | 76 | 85 | 975 | — |
| Aliette | | 45 | 85 | 98 | 99 | 245 | — |
| Cymoxanil | | 0 | 20 | 58 | 72 | 1229 | — |
| BABA + Aliette + Cymoxanil | 60 + 25 + 15 | 63 | 70 | 88 | 95 | 584 | 1.0 |
| | 25 + 60 + 15 | 70 | 85 | 98 | 100 | 100 | 3.4 |

[a] Control plants were 100% infected

TABLE 22

CONTROL OF DOWNEY MILDEW IN CUCUMBER BY BABA, MANCOZEB, CYMOXANIL AND THEIR MIXTURES

| Compounds | Ratio | Percent Disease Control[a] mg/L Active Ingredient | | | | | $ED_{90}$ mg/L | CF |
|---|---|---|---|---|---|---|---|---|
| | | 4 | 16 | 62 | 250 | 1000 | | |
| BABA | | — | 0 | 13 | 50 | 63 | 1413 | — |
| Mancozeb | | 75 | 87 | 90 | 92 | — | 167 | — |
| Cymoxanil | | 13 | 25 | 38 | 50 | — | 506 | — |
| BABA + Mancozeb + Cymoxanil | 60 + 25 + 15 | 63 | 75 | 83 | 95 | | 152 | 3.0 |
| | 25 + 60 + 15 | 75 | 87 | 90 | 95 | | 136 | 1.8 |

[a] Control plants were 100% infected

TABLE 23

CONTROL OF DOWNY MILDEW IN CUCUMBER BY BABA, BAYER SZX (FENCARAMID) AND THEIR MIXTURES

| Compounds | Ratio | Percent Disease Control[b] @ mg/L Active Ingredient | | | | | | | $ED_{90}$ mg/L | CF |
|---|---|---|---|---|---|---|---|---|---|---|
| | | 2 | 8 | 31 | 125 | 500 | 1000 | 2000 | | |
| BABA | | | | | | 61 | 72 | 74 | 2354 | |
| FENCARAMID | | 78 | 83 | 95 | 100 | | | | 19 | |
| BABA + FENCARAMID | 80 + 20 | 38 | 58 | 83 | 100 | | | | 33 | 2.8 |
| | 50 + 50 | 60 | 80 | 98 | 100 | | | | 14 | 2.7 |
| | 20 + 80 | 78 | 85 | 98 | 100 | | | | 13 | 1.8 |

[a] 5 days post innoculation
[b] Control plants were 81% infected

TABLE 24

CONTROL OF DOWNY MILDEW IN CUCUMBER BY BABA, BAYER DIMETHOMORPH (DMN) AND THEIR MIXTURES

| Compounds | Ratio | Percent Disease Control[b] @ mg/L Active Ingredient |
|---|---|---|
| BABA 1000 | gave | 17% Control |
| DMN 5 ppm | gave | 32% Control |
| BABA + DMN 1000 + 5 ppm | gave | 74% Control |

$$\text{Synergy ratio} = \frac{74 = 74}{17 = 32 - \frac{(17\;32)\;33}{100}}$$

$$= 2.24$$

TABLE 25

CONTROL OF DOWNY MILDEW IN CUCUMBER BY BABA, FOLPET, CYMOXANIL AND THEIR MIXTURES[a]

| Compounds | Ratio | Percent Disease Control[b] mg/L @ Active Ingredient | | | | $ED_{90}$ mg/L | CF |
|---|---|---|---|---|---|---|---|
| | | 16 | 62 | 250 | 1000 | | |
| BABA | | 6 | 22 | 48 | 82 | 1072 | |
| FOLPET | | 43 | 84 | 95 | 97 | 403 | |
| | | 48 | 63 | 82 | 97 | 524 | |
| BABA + FOLPET + CYMOXANIL | 25 + 60 + 15 | 76 | 87 | 95 | 99 | 247 | 2.0 |

[a] 5 days post inoculation
[b] Control plants were 95% infected

TABLE 26

CONTROL OF DOWNY MILDEW IN CUCUMBER BY BABA PHOSETYL-ALUMINIUM AND THEIR MIXTURES[a]

| Compounds | Ratio | Percent Disease Control[b] mg/L Active Ingredient | | | | $ED_{90}$ mg/L | CF |
|---|---|---|---|---|---|---|---|
| | | 16 | 62 | 250 | 1000 | | |
| BABA | | 10 | 43 | 43 | 71 | 1386 | — |
| Phosetyl-Aluminium | | 71 | 71 | 94 | 86 | 638 | — |
| BABA + | 12 + 88 | 43 | 43 | 86 | 100 | 261 | 4.7 |
| Phosetyl-Aluminium | 25 + 75 | 0 | 14 | 71 | 97 | 551 | 1.9 |
| | 50 + 50 | 0 | 14 | 57 | 83 | 1009 | 0.9 |
| | 75 + 25 | — | 57 | 57 | 86 | 918 | 0.8 |
| | 88 + 12 | 14 | 29 | 71 | 86 | 931 | 0.7 |

[a] 7 days post innoculation
[b] control plants were 88% infected

TABLE 27

CONTROL OF LATE BLIGHT IN POTATO BY BABA, BION AND THEIR MIXTURES[a]

| Compounds | Ratio (w/w) | Percent Disease Control mg/L Active Ingredient | | | $ED_{90}$ mg/L | CF |
|---|---|---|---|---|---|---|
| | | 250 | 500 | 1000 | | |
| BABA | | 38 | 75 | 93 | 776 | — |
| BION | | 13 | 25 | 78 | 1173 | — |
| BABA + ACIBENZOLAR-S-METHYL (10 + 1) | | 38 | 78 | 98 | 639 | 1.3 |

TABLE 28

CONTROL OF LATE BLIGHT IN TOBACCO BY BABA AZOXYSTROBINE MIXTURE AND THEIR MIXTURES, FUNGAL ISOLATE = R

| Compounds | Ratio (w/w) | Percent Disease Control mg/L Active Ingredient | | | | | | $ED_{90}$ mg/L | CF |
|---|---|---|---|---|---|---|---|---|---|
| | | 5 | 10 | 25 | 50 | 100 | 200 | | |
| BABA | — | — | — | — | 0 | 13 | 100 | 171 | |
| AZOXY-STROBINE | 13 | 81 | 81 | 81 | 93 | — | — | 27 | |
| BABA + AZOXY-STROBINE | | | | | | | | | |
| 5 + 1 | | 25 | 100 | 100 | 100 | | | 41 | 2.2 |
| 10 + 1 | | 38 | 81 | 100 | 100 | | | 54 | 2.1 |
| 15 + 1 | | 50 | 81 | 100 | 100 | | | 53 | 2.4 |

TABLE 29

CONTROL OF DOWNY MILDEW IN TOBACCO BY BABA, ACIBENZOLAR-S-METHYL, RIDOMIL-GOLD AND THEIR MIXTURES: Fungal isolate = R

| Compounds | Ratio (w/w) | Percent Disease Control mg/L Active Ingredient | | | $ED_{90}$ mg/L | CF |
|---|---|---|---|---|---|---|
| | | 16 | 62 | 250 | | |
| BABA | — | 3 | 27 | 51 | 406 | |
| BION | — | 76 | 76 | 99 | 88 | |
| RIDOMILGOLD | — | 49 | 37 | 58 | 416 | |

TABLE 29-continued

CONTROL OF DOWNY MILDEW IN TOBACCO BY BABA, ACIBENZOLAR-S-METHYL, RIDOMIL-GOLD AND THEIR MIXTURES: Fungal isolate = R

| Compounds | Ratio (w/w) | Percent Disease Control mg/L Active Ingredient | | | $ED_{90}$ mg/L | CF |
|---|---|---|---|---|---|---|
| | | 16 | 62 | 250 | | |
| BABA + ACIBENZOLAR-S-METHYL | 75 + 1 | 48 | 78 | 99 | 90 | 3.1 |
| | 10 + 1 | 45 | 93 | 100 | 52 | 5.9 |
| | 15 + 1 | 22 | 84 | 91 | 186 | 1.8 |
| | 20 + 1 | 14 | 74 | 98 | 116 | 3.5 |
| BABA + RIDOMIL GOLD | 7.5 + 1 | 27 | 63 | 97 | 150 | 2.7 |
| | 10 + 1 | 34 | 44 | 99 | 145 | 2.8 |
| | 15 + 1 | 23 | 52 | 78 | 282 | 1.4 |
| | 20 + 1 | 0 | 20 | 91 | 239 | 1.4 |
| BABA + ACIBENZOLAR-S-METHYL + RIDOMIL-GOLD | 7.5 + 1 + 1 | 37 | 63 | 95 | 174 | 1.7 |
| | 10 + 1 + 1 | 45 | 71 | 92 | 190 | 1.7 |
| | 15 + 1 + 1 | 37 | 84 | 82 | 230 | 1.5 |
| | 20 + 1 + 1 | 57 | 98 | 98 | 84 | 4.2 |

TABLE 30

CONTROL OF DOWNY MILDEW IN TOBACCO BY BABA, ACIBENZOLAR-S-METHYL, CURZATE RIDOMIL-GOLD AND THEIR MIXTURES: Fungal isolate = R

| Compounds | Ratio (w/w) | Percent Disease Control mg/L Active Ingredient | | | $ED_{90}$ mg/L | CF |
|---|---|---|---|---|---|---|
| | | 100 | 200 | 400 | | |
| BABA | — | 37 | 62 | 100 | 270 | — |
| ACIBENZOLAR-S-METHYL | — | 37 | 50 | 80 | 443 | — |
| CURZATE | — | 25 | 25 | 62 | 596 | — |
| RIDOMILGOLD | — | 20 | 35 | 42 | >1000 | — |
| BABA + ACIBENZOLAR-S-METHYL | 10 + 1 | 62 | 100 | 100 | 113 | 2.5 |
| | 15 + 1 | 50 | 100 | 100 | 118 | 2.3 |
| BABA + CURZATE | 10 + 1 | 62 | 100 | 100 | 113 | 2.5 |
| | 5 + 1 | 37 | 62 | 100 | 270 | 1.1 |

TABLE 31

CONTROL OF DOWNY MILDEW IN TOBACCO BY BABA, ACIBENZOLAR-S-METHYL, RIDOMIL-GOLD AND THEIR MIXTURES: Fungal isolate = S

| Compounds | Ratio (w/w) | Percent Disease Control mg/L Active Ingredient | | | $ED_{90}$ mg/L | CF |
|---|---|---|---|---|---|---|
| | | 0.5 | 5 | 50 | | |
| BABA | — | 0 | 27 | 59 | 78 | — |
| ACIBENZOLAR-S-METHYL | — | 54 | 76 | 85 | 52 | — |
| RIDOMILGOLD | | 100 | 100 | 100 | 0.2 | — |
| BABA + ACIBENZOLAR-S-METHYL | 7.5 + 1 | 85 | 85 | 99 | 15 | 4.9 |
| | 10 + 1 | 86 | 94 | 100 | 4 | 18.7 |
| | 15 + 1 | 75 | 84 | 100 | 5 | 15.1 |
| BABA + RIDOMIL-GOLD | 7.5 + 1 | 94 | 100 | 100 | 0.5 | 3.3 |
| | 10 + 1 | 99 | 100 | 100 | 0.4 | 5.4 |
| | 15 + 1 | 88 | 90 | 100 | 4.3 | 2.1 |
| BABA + ACIBENZOLAR-S-METHYL + RIDOMIL-GOLD | 7.5 + 1 + 1 | 99 | 100 | 100 | 0.4 | 4.4 |
| | 10 + 1 + 1 | 100 | 100 | 100 | 0.2 | 12.2 |
| | 15 + 1 + 1 | 73 | 100 | 100 | 0.6 | 5.3 |

TABLE 32

CONTROL OF DOWNY MILDEW IN GRAPES BY BABA ACIBENZOLAR-S-METHYL AND THEIR MIXTURES IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 0.31 | 1.25 | 5 | 20 | 50 | 100 | | |
| BABA | | — | — | 15 | 93 | 95 | 99 | 38 | — |
| ACIBENZOLAR-S-METHYL | 0 | 27 | 75 | 100 | — | — | | 6 | — |
| BABA + ACIBENZOLAR-S-METHYL | 10 + 1 | 0 | 37 | 68 | 100 | — | — | 6.6 | 3.9 |
| | 15 + 1 | 60 | 82 | 100 | 100 | — | — | 1.4 | 19.8 |

TABLE 33

CONTROL OF DOWNY MILDEW IN GRAPES BY BABA, ALLIETTE AND THEIR MIXTURES IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 1.25 | 2.5 | 5 | 10 | 20 | 50 | | |
| BABA | | — | 38 | 44 | 81 | 86 | 92 | 33 | — |
| ALLIETTE | 13 | 36 | 38 | 40 | 48 | 81 | — | 24 | |
| BABA + ALLIETTE | 1 + 1 | 44 | 81 | 87 | 89 | 92 | — | 12 | 2.3 |
| | 3 + 1 | 44 | 69 | 88 | 92 | 95 | — | 10 | 3.0 |
| | 5 + 1 | 25 | 31 | 43 | 47 | 83 | — | 22 | 1.4 |
| | 7 + 1 | 24 | 31 | 34 | 56 | 62 | — | 30 | 1.0 |
| | 9 + 1 | 22 | 34 | 39 | 55 | 61 | — | 31 | 1.0 |

TABLE 34

CONTROL OF DOWNY MILDEW IN GRAPES BY BABA, CURZATE AND THEIR MIXTURES, IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 1.25 | 2.5 | 5 | 10 | 20 | 50 | | |
| BABA | — | — | 25 | 36 | 78 | 83 | 91 | 36 | — |
| CURZATE | | 11 | 39 | 58 | 66 | 55 | — | 27 | — |
| BABA + CURZATE | 1 + 1 | 51 | 61 | 68 | 81 | 89 | — | 16 | 1.9 |
| | 3 + 1 | 62 | 70 | 77 | 86 | 93 | — | 13 | 2.6 |
| | 5 + 1 | 69 | 74 | 81 | 89 | 95 | — | 11 | 3.1 |
| | 7 + 1 | 49 | 68 | 74 | 78 | 89 | — | 16 | 2.2 |
| | 9 + 1 | 21 | 39 | 58 | 73 | 82 | — | 17 | 2.1 |

What is claimed is:

1. A synergistic fungicidal composition comprising synergistically effective respective amounts of (1) D,L-3-aminobutyric acid or the n-octyl ester thereof, together with (2) copper or a copper salt.

2. The fungicidal composition of claim 1, wherein said copper salt is copper sulfate, copper hydrate or copper sulfate hydrate.

3. The fungicidal composition of claim 1 wherein the (1) D,L-β-aminobutyric acid or n-octyl ester thereof and (2) copper or a copper salt are present in a weight ratio within a range of 4:1 to 1:4.

4. The fungical composition of claim 1 wherein fungicidal components consist essentially of said (1) D,L-3-aminobutyric acid or n-octyl ester thereof and (2) said copper or a copper salt.

5. A method of administering a fungicidal composition in accordance with claim 1 to a plant infested with a fungus, wherein the fungus is selected from the group consisting of Phytophthora infestans, Pseudopersonspora Cubensis, Plasmopara veticola, and Peronospora tabacina.

6. The method of claim 5 wherein the fungus is selected from the group consisting of Phytophthora infestans in potatoes and tomatoes, Pseudoperonspora Cubensis in cucumber and melons, Plasmopara veticola in grapes, and Peronospora tabacina in tobacco.

7. A method of controlling fungal infections in plants comprising applying to the plants or parts thereof a synergistic fungicidal composition comprising synergistically effective respective amounts of (1) D,L-3-aminobutyric acid or the n-octyl ester thereof, and (2) copper or a copper salt.

8. The method of claim 7 wherein said copper salt is copper sulfate, copper hydrate or copper sulfate hydrate.

9. The method of claim 7 which comprises applying said (1) D,L-3-aminobutyric acid or n-octyl ester thereof and (2) said copper or a copper salt in a weight ratio within a range of 4:1 to 1:4.

10. The method of claim 7 wherein the plants are selected from the group consisting of potatoes, tomatoes, cucumbers, melons, grape vines and tobacco.

* * * * *